United States Patent [19]
Elliott et al.

[11] Patent Number: 5,716,985
[45] Date of Patent: Feb. 10, 1998

[54] ENDOTHELIN RECEPTOR ANTAGONISTS

[75] Inventors: John Duncan Elliott, Wayne; Maria Amparo Lago, Audubon, both of Pa.

[73] Assignee: SmithKline Beecham Corporation, Philadelphia, Pa.

[21] Appl. No.: 450,938

[22] Filed: May 23, 1995

Related U.S. Application Data

[63] Continuation-in-part of Ser. No. 336,444, filed as PCT/US92/09427, Oct. 29, 1992, which is a continuation-in-part of Ser. No. 66,818, filed as PCT/US94/04603, Apr. 26, 1994, abandoned, which is a continuation-in-part of Ser. No. 854,195, Mar. 20, 1992, abandoned, which is a continuation-in-part of Ser. No. 787,870, Nov. 5, 1991, abandoned.

[51] Int. Cl.$^6$ .......................... A61K 31/36; A61K 31/44; A61K 31/335; A61K 31/19

[52] U.S. Cl. ............... 514/464; 514/84; 514/92; 514/100; 514/277; 514/337; 514/338; 514/381; 514/382; 514/443; 514/450; 514/452; 514/464; 514/465; 514/517; 514/530; 514/569

[58] Field of Search .................. 549/362, 438, 549/441, 444, 447, 427, 349, 359, 433, 350, 435, 462, 30; 548/253, 454, 488, 526; 546/22, 256, 267, 268.1, 282.4, 283.7, 342; 514/84, 92, 100, 277, 337, 338, 381, 382, 443, 450, 452, 464, 465, 517, 530, 569

[56] References Cited

PUBLICATIONS

Ohlstein et al., Proc. Natl. Acad. Sci. USA, vol. 91, pp. 8052–8056 (1994).

*Primary Examiner*—Nicky Chan
*Attorney, Agent, or Firm*—Linda E. Hall; Stephen A. Venetianer; Edward T. Lentz

[57] ABSTRACT

Novel indane and indene derivatives are described which are endothelin receptor antagonists.

7 Claims, No Drawings

ENDOTHELIN RECEPTOR ANTAGONISTS

This is a continuation-in-part of application Ser. No. 08/336,444, filed on Nov. 9, 1994 which is a a continuation-in-part of PCT/US94/04603 filed on Apr. 26, 1994 which is a continuation-in part of Ser. No. 08/066,818 filed on Apr. 27, 1993, now abandoned, which is a continuation-in-part of PCT/US92/09427 filed on Oct. 29, 1992, which is a continuation-in-part of Ser. No. 07/854, 195 filed on Mar. 20, 1992, now abandoned, which is a continuation-in-part of Ser. No. 07/787,870 filed on Nov. 5, 1991, now abandoned.

FIELD OF INVENTION

The present invention relates to novel indane and indene derivatives, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarcdon, subaraclmoid hemorrhage, atherosderosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99:597–601, 1989 and Clozel and Clozel, Circ. Res., 65:1193–1200, 1989) coronary vasospasm (Fukuda et at., Eur. J. Pharm. 165:301–304, 1989 and Lüscher, Circ. 83:701, 1991) heart failure, proliferation of vascular smooth muscle cells, (Takagi, Biochem & Biophys. Res. Commun.; 168:537–543, 1990, Bobek et at., Am. J. Physiol. 258:408–C415, 1990) and atherosclerosis, (Nakaki et at., Biochem. & Biophys. Res. Commun. 158:880–881, 1989, and Lerman et al., New Eng. J. of Med. 325:997–1001, 1991). Increased levels of endothelin have been shown after coronary balloon angioplasty (Kadel et at., No. 2491 Circ. 82:627, 1990).

Further, endothelin has been found to be a potent constrictor of isolated mammalian airway tissue including human bronchus (Uchida et al., Eur J. of Pharm. 154:227–228 1988, LaGente, Clin. Exp. Allergy 20:343–348, 1990; and Springall et at., Lancet, 337:697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et at., Supra, p. 112.

Endothelin has been associated with the induction of hemorrhagic and necrotic damage in the gastric mucosa (Whittle et at., Br. J. Pharm. 95:1011–1013, 1988); Raynaud's phenomenon, Cinniniello et at., Lancet 337:114–115, 1991); Crohn's Disease and ulcerative colitis, Munch et al., Lancet, Vol. 339, p. 381; Migraine (Edmeads, Headache, February 1991 p 127); Sepsis (Weitzberg et at., Circ. Shock 33: 222–227, 1991; Pittet et al., Ann. Surg. 213:262–264, 1991), Cyclosporin-induced renal failure or hypertension (Eur. J. Pharmacol., 180: 191–192, 1990, Kidney Int, 37:1487–1491, 1990) and endotoxin shock and other endotoxin induced diseases (Biochem, Biophys. Res. Commun., 161: 1220–1227, 1989, Acta Physiol. Scand. 137:317–318, 1989) and inflammatory skin diseases, (Clin Res. 41:451 and 484, 1993) and macular degeneration.

Endothelin has also been implicated in preclampsia of pregnancy. Clark et at., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio. 40 (1991) 215–220; Schiff et at,, Am. J. Obstet. Gynecol. February 1992, p. 624–628; diabetes mellitus, Takahashi et at., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported 16 stimulate the transport of sperm in the uterine cavity, Casey et at., J. Clin. Endo and Metabolism, Vol. 74, No. 1, p. 223–225, therefore endothelin antagonists may be useful as male contraceptives. Endothelin modulates the ovariarn/menstrual cycle, Kenegsberg, J. of Clin. Endo. and Met., Vol. 74, No. 1, p. 12, and may also play a role in the regulation of penile vascular tone in man, Lau et at., Asia Pacific J. of Pharm., 1991, 6:287–292 and Tejada et at., J. Amer. Physio. Soc. 1991, H1078–H1085. Endothelin also mediates a potent contraction of human prostatic smooth muscle, Langenstroer et at., J. Urology, Vol. 149, p. 495–499.

Thus, endothelin receptor antagonists would offer a unique approach toward the pharmacotherapy of hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, congestive heart failure, asthma, pulmonary hypertension, pulmonary hypertension secondary to intrinsic pulmonary disease, atherosclerosis, macular degeneration, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention or treatment of restenosis, diabetes, preclampsia of pregnancy, bone remodeling, kidney transplant, male contraceptives, infertility and priaprism and benign prostatic hypertrophy.

SUMMARY OF THE INVENTION

This invention comprises indane and indene derivatives represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure, atherosclerosis, pulmonary hypertension, pulmonary hypertension secondary to intrinsic pulmonary disease, and as an adjunct in angioplasty for prevention of restenosis and benign prostatic hypertrophy.

This invention further constitutes a method for antagonizing endothelin receptors in an animal, including humans, which comprises administering to an animal in need thereof an effective amount of a compound of Formula (I).

Specifically (+)-(1S, 2R, 3S)-3-[2-(2-hydroxyeth-1-yloxy)-4-methoxyphenyl]-1-(3,4-methylenedioxyphenyl)-5-propoxyindane-2-carboxylic acid has been shown to be orally bioavailable in comparison to (+)(1S, 2R, 3S)-3-(2-carboxymethoxy-4-methoxyphenyl)-1-(3,4-methylenedioxyphenyl)-5-(prop-1-yloxy)-indane-2-carboxylic acid.

DETAILED DESCRIPTION OF THE INVENTION

The compounds of this invention are represented by structural Formula (I):

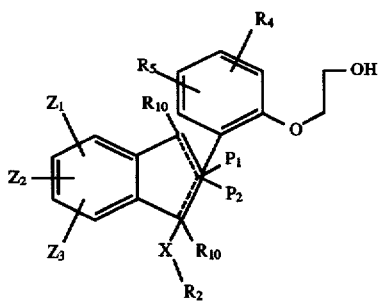

(I)

wherein:

$R_2$ is hydrogen, Ar, $C_{1-4}$alkyl or

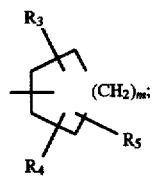

(c)

$P_1$ is —$X(CH_2)_nR_8$;

$P_2$ is —$X(CH_2)_nR_8$, or —X—$R_9$—Y;

$R_3$ and $R_5$ are independently hydrogen, $R_{11}$, OH, $C_{1-8}$alkoxy, $S(O)_qR_{11}$, $N(R_6)_2$, Br, F, I, Cl, $CF_3$, $NHCOR_6$, $R_{13}CO_2R_7$, —X—$R_9$—Y, or —$X(CH_2)_nR_8$ wherein each methylene group within —$X(CH_2)_nR_8$ may be unsubstituted or substituted by one or two —$(CH_2)_n$Ar groups;

$R_4$ is hydrogen, $R_{11}$, OH, $C_{1-5}$alkoxy, $S(O)_qR_{11}$, $N(R_6)_2$, Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-10}$alkyl, $C_{2-10}$alkenyl or $C_{2-8}$ alkynyl, all of which may be unsubstituted or substituted by one or more OH, $N(R_6)_2$, $CO_2R_{12}$, halogen or $XC_{1-5}$alkyl; or $R_7$ is $(CH_2)nAr$;

$R_8$ is hydrogen, $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, —$CO_2(CH_2)_mC(O)N(R_6)_2$, $C(R_{11})_2N(R_7)_2$, $C(O)N(R_6)_2$, tetrazole or $OR_6$;

$R_9$ is a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R_6)_2$, COOH or halogen;

$R_{10}$ is $R_3$ or $R_4$;

$R_{11}$ is hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is hydrogen, $C_{1-6}$alkyl, $C_{2-6}$alkenyl or $C_{2-7}$alkynyl;

$R_{13}$ is divalent Ar, $C_{1-10}$alkylene, $C_{1-10}$alkylidene, $C_{2-10}$alkenylene, $C_{2-10}$ alkynylene, all of which may be unsubstituted or substituted by one or more OH, $CH_2OH$, $N(R_6)_2$ or halogen;

X is $(CH_2)_n$, O, $NR_6$ or $S(O)_q$;

Y is $CH_3$ or $X(CH_2)_n$Ar;

Ar is:

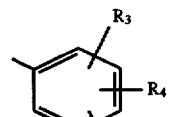

(a)

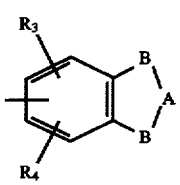

(b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or $(C(R_6)_2)_m$;

B is —$CH_2$— or —O—;

$Z_1$ and $Z_2$ are independently hydrogen, $C_{1-8}$alkyl, $C_{2-8}$alkenyl, $C_{2-8}$alkynyl, OH, $C_{1-8}$alkoxy, $S(O)qC_{1-8}$alkyl, $N(R_6)_2$, Br, F, I, Cl, $NHCOR_6$, —X—$R_9$—Y, —$X(CH_2)_nR_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_nCH_3$, $CO(CH_2)_nCH_2N(R_6)_2$, or halogen; or $Z_1$ and $Z_2$ together may be —O—A—O— on contiguous carbons;

$Z_3$ is $Z_1$ or —X—$R_9$—Y;

q is zero, one or two;

n is an integer from 0 to six;

m is 1, 2 or 3; and the dotted line indicates the optional presence of a double bond; or a pharmaceutically acceptable salt thereof; provided that $R_2$ is not hydrogen when X is $S(O)_q$;

when the optional double bond is present there is only one $R_{10}$ and there is no $P_1$ and $P_2$ is not $NR_6R_9Y$; and if X—$R_2$ is attached to the double bond, X is not $NR_6$; and when $R_3$, $R_5$, $Z_1$, $Z_2$, or $Z_3$ is $X(CH_2)_nR_8$ and n is not O, X is oxygen or $NR_6$ when $R_8$ is $OR_6$ or $CO_2H$.

Also included in the invention are pharmaceutically acceptable salt complexes. Preferred are the ethylene diamine, sodium, potassium, calcium and ethanolamine salts.

The term alkylene is a divalent alkyl group in which the bonds are on two different carbon atoms; alkylidene is a divalent alkyl group in which the bonds are on the same carbon atom; alkenylene is a divalent alkene group in which the bonds may be on any carbon atom; alkynylene is a divalent alkynyl group in which the bonds may be on any carbon atom.

All alkyl, alkenyl, alkynyl, alkoxy, alkylene, alkylidene, alkenylene and alkynylene groups may be straight or branched. The term "halogen" is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

Preferred compounds are those wherein $R_2$ is a moiety of formula (a) or (b), $C_{1-4}$alkyl, indolyl or hydrogen; $R_3$ and $R_5$ are independently hydrogen, OH, $C_{1-5}$alkoxy, halogen, —$OC_{1-4}$alkyl phenyl, $R_{13}CO_2R_7$, $C_{1-4}$alkyl, $N(R_6)_2$, $NH(CO)CH_3$, —$X(CH_2)_nR_8$, —$X$—$R_9$—$Y$ pyridyl, phenyl or $S(O)_qC_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_pC_{1-5}$alkyl; $Z_1$, $Z_2$ and $Z_3$ are independently $XR_9Y$, benzyl, hydrogen, OH, $C_{1-5}$alkoxy, —$N(R_6)_2$, $S(O)qC_{1-8}$alkyl, $NHCOR_6$, $X(CH_2)_nR_8$ or halogen, or $Z_1$ and $Z_2$ together may be —O—A—O on contiguous carbons; $P_1$ and $P_2$ are independently hydrogen, $CO_2H$, $C(R_6)_2CO_2H$ or tetrazole; Ar is a moiety of formula (a) or (b), phenyl, or pyridyl; X is $(CH_2)_n$ or oxygen.

More preferred are compounds wherein $R_3$ is hydrogen, —$X(CH_2)_nR_8$ or $R_{13}CO_2R_7$; $R_5$ are independently hydrogen, OH, $C_{1-5}$alkoxy, $SC_{1-5}$alkyl, substituted phenyl, F, Br, $C_{1-3}$alkyl or $NH_2$; $R_4$ is hydrogen, OH, $C_{1-5}$alkoxy or $SC_{1-5}$alkyl, $Z_1$ and $Z_3$ are hydrogen and $Z_2$ is hydrogen, OH, $C_{1-5}$alkoxy, halogen, $X(CH_2)_nR_8$, $NH_2$, benzyl, $NH(CO)CH_3$, or $Z_1$ and $Z_2$ together may be O—A—O on contiguous carbons and $R_2$, $P_1$, $P_2$, Ar and X are as above for preferred compounds.

Most preferred are compounds wherein $R_2$ is (a) or (b); A is $CH_2$, B is —O—; there is no optional double bond; $Z_2$ is hydrogen, OH, $C_{1-5}$alkoxy, or —$OCH_2CH=CH_2$, $Z_1$ is hydrogen; $R_3$ is XAr, hydrogen, $X(CH_2)_nCOOH$, $X(CH_2)_nCONR_7SO_2R_{11}$, $X[(CR_6)_2]_nOR_6$ or $CH=CHCO_2H$; $R_5$ is hydrogen, substituted phenyl, pyddyl or pyrimidyl, or $C_{1-2}$alkoxy; $R_4$, $R_{10}$ and $P_2$ are hydrogen, and $P_1$ is $CO_2H$ or $C(R_6)_2CO_2H$.

Especially preferred are compounds wherein $R_2$ is (a); A is $CH_2$, B is —O—; there is no optional double bond; the phenyl ring and $XR_2$ are trans to $P_1$; X is a bond; $Z_1$ and $Z_3$ are hydrogen; $Z_2$ is hydrogen, OH or $C_{1-5}$alkoxy; $R_3$ is hydrogen, OAr (where Ar is (a), (b), pyridyl or pyrimidyl and A is $CH_2$ and B is —O— and Ar may be substituted by $CO_2H$), $O(CH_2)_{1-3}CO_2H$, $O(CH_2)_{1-3}CONHSO_2R_{11}$, $(CH_2)_{0-4}CO_2H$, $(CH_2)_{0-3}CONH SO_2R_{11}$, or $O[(CR_6)_2]_{2-4}OH$; $R_5$ is hydrogen, $C_{1-2}$alkoxy, or phenyl, pyridyl or pyrimidyl all of which may be substituted by $R_3$ or $C_{1-2}$alkoxy; $R_4$, $R_{10}$ and $P_2$ are hydrogen; and $P_1$ is $CO_2H$ or $CH_2CO_2H$.

Especially preferred compounds are the following:

(+)(1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylate;

(1RS, 2SR, 3RS)-3-[2-(2-Hydroxyeth-1-yloxy)-4-methoxyphenyl]-1-(3,4-methylenedioxyphenyl)-5-(prop-1-yloxy)indane-2-carboxylate;

(+)(1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylate hemiethylenediamine salt;

(+)(1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylate sodium salt;

(1RS, 2SR, 3RS)-3-[2-(2-Hydroxyeth-1-yloxy)-4-methoxyphenyl]-1-(3,4-methylenedioxyphenyl)-5-(prop-1-yloxy)indan-2-yl acetic acid.

The present invention provides compounds of Formula (I) above

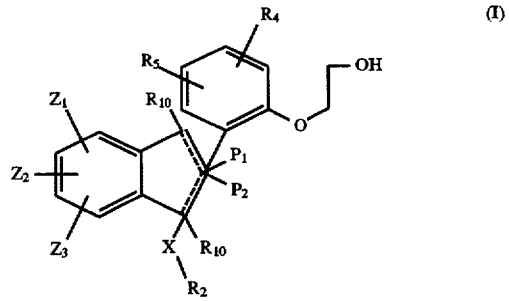

which can be prepared by a process which comprises:

a) reacting a compound of Formula (2) wherein X is $C_{1-5}$alkyl

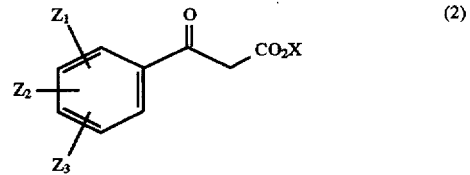

with a substituted benzaldehyde or aldehyde of Formula (3).

wherein D is Ar or (c) as defined in Formula I, in a suitable solvent such as benzene with a catalyst such as piperidinium acetate at reflux to provide a compound of Formula (4).

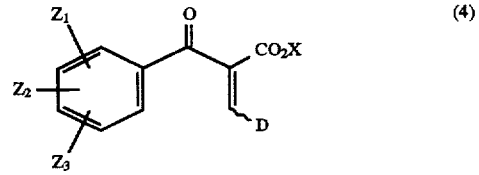

Cyclization of compound (4) in the presence of a suitable Lewis acid such as titanium tetracholoride or aluminum chloride or alternatively when $Z_1$ is 3-OR (meta)(where R is $C_{1-5}$alkyl, or benzyl), trifluoroacetic acid, provides an indanone of the Formula (5).

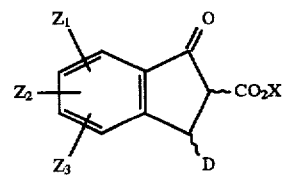

Dehydrogenation with 2,3-dichloro-5,6-dicyano-1,4-benzoquinone in an appropriate solvent or alternatively bromination with pyridinium hydrobromide perbromide in dichloromethane followed by treatment with 1,5-diazabicyclo[4.3.0]non-5-ene provides inclenones of Formula (6).

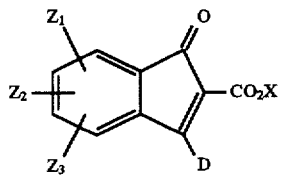

b) Alternatively, a compound of Formula 6 wherein $Z_1$, $Z_2$ and $Z_3$ are hydrogen and

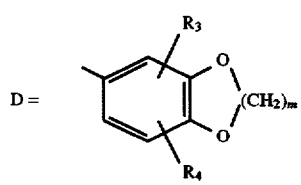

can be prepared by treatment of 2-bromobenzoic acid with two equivalents of n-butyllithium in a solvent such as tetrahydrofuran under argon at −78° C. followed by the addition of an acid chloride of Formula (7):

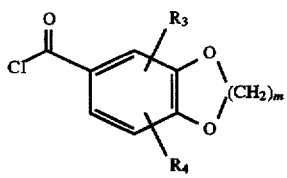

provides a compound of Formula (8):

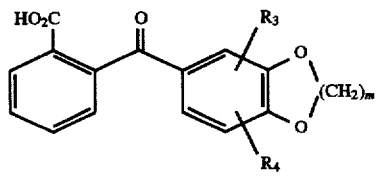

Treatment of compounds of type (8) with thionyl chloride at reflux gives an acid chloride which can be isolated by concentration under reduced pressure. This acid chloride can then be treated with diethyl magnesium malonate in a solvent such as ether to give a compound of Formula (9):

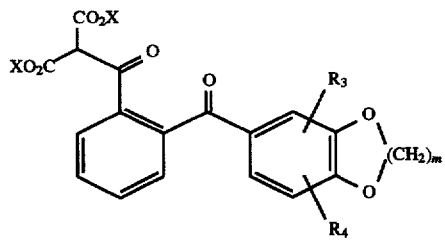

Reaction of a compound of type (9) at reflux with 5% aqueous sodium carbonate gives compounds of Formula (10):

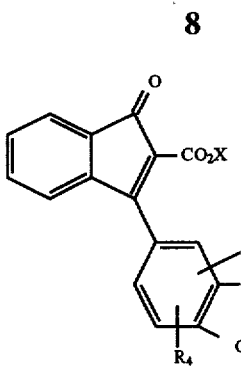

c) Treatment of an indenone of Formula (11):

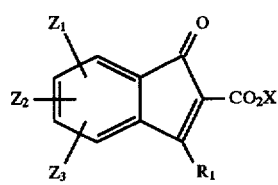

wherein $Z_1$, $Z_2$, and $Z_3$ are as defined for formula I or a group convertable to them, with an organomagnesium compound of Formula (12) wherein $R_2$ is defined for $$R_2(CH_2)_nMgBr \qquad (12)$$

Formula I or a group convertable to it, in a suitable solvent provides compounds of Formula (13):

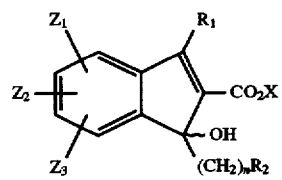

wherein $R_1$ is

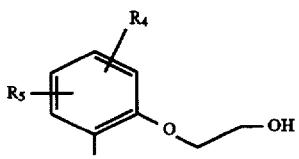

Saponification of compounds of Formula (13) using sodium hydroxide in aqueous methanol followed by reduction with triethylsilane and boron trifluoride etherate in a suitable solvent such as dichloromethane at 0° C. affords racemic compounds of Formula (14).

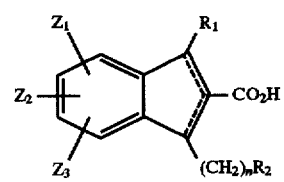

Conjugate addition of nucleophiles to an ester derived from Formula (14), followed by saponification affords compounds of Formula (I) having an $R_{10}$ other than hydrogen. Re-introduction of a double bond into an ester derived from such acids followed by conjugate addition of another nucleophilic species and subsequent saponification affords compounds of Formula (1) in which neither $R_{10}$ substituent is hydrogen.

Reduction of compounds of Formula (13) with triethylsilane and boron trifluoride etherate in a suitable solvent such as dichloromethane at 0° C. followed by hydrogenation with hydrogen gas under pressure at approximately 60 psi in the presence of a suitable catalyst such as 10% palladium on charcoal affords compounds of Formula (15):

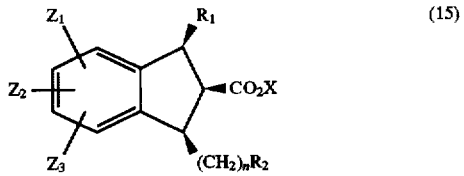

(15)

Alkylation or acylation of the ester enolate derived from Formula (15) affords compounds wherein $P_1$ and $P_2$ are as defined in Formula (1).

Alternatively, hydrogenation of compounds of Formula (13) with hydrogen gas under pressure at approximately 60 psi in the presence of a suitable catalyst such as 10% palladium on charcoal in a suitable solvent such as ethyl acetate or methanol containing 1–5% acetic acid affords compounds of Formula (15). Treatment of these compounds with a base such as sodium hydroxide in a suitable solvent such as aqueous ethanol provides racemic compounds of Formula (16):

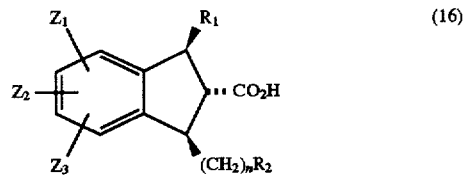

(16)

wherein $Z_1$, $Z_2$ and $Z_3$ are hydrogen; $R_1$ is as defined previously and $R_1=R_2$; and n is 0. Treatment of compounds of Formula (13) with triethylsilane and boron trifluoride etherate in a suitable solvent such as dichloromethane at 0° C. followed by reaction with samarium II iodide in a suitable solvent such as tetrahydrofuran and then saponification, provides compounds of Formula (17)

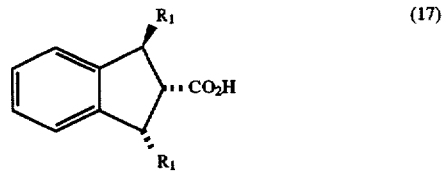

(17)

With appropriate manipulation and protection of any chemical functionalities, synthesis of the remaining compounds of the Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/FKg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation (Rat Cerebellum or Kidney Cortex)

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000 xg for 10 minutes at 4° C. The supernatant was removed and centrifuged at 40,000 xg for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 micrograms of protein for each tube for cerebellum and kidney cortex in the binding assay.

Freshly isolated rat roesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000 xg for 10 min. at 4° C. The supernatant was removed and centrifuged at 40,000 xg for 30 min. at 4° C. The resulting pellet was resuspended as explained above for cerebellum and kidney cortex. Approximately 10 micrograms of membrane protein was used for each tube in binding experiments.

B) CHO Cell Membrane Preparation

CHO cells stably transfected with human $ET_A$ and $ET_B$ receptors were grown in 245 mm×245 mm tissue culture plates in Dulbecco's modified Eagle's medium (DMEM) supplemented with 10% fetal bovine serum (FBS). The confluent cells were washed with DPBS (Dulbecco's phosphate buffered saline) containing protease inhibitor cockatil (5 mM EDTA, 0.5 mM PMSF, 5 ug/ml leupeptin, and 0.1 U/ml aprotinin) and scraped in the same buffer. After centrifugation at 800 xg, the cells were lysed by freezing in liquid nitrogen and thawing on ice followed by homogenization (30 times using glass dounce homogenizer) in lysis buffer containing 20 mM Tris HCl, pH 7.5 and the protease inhibitor cocktail. Mter an initial centrifugation at 800 xg for 10 min to remove unbroken cells and nuclei, the supernatants were centrifuged at 40,000 xg for 15 min and the pellet was resuspended in 50 mM Tris HCl, pH 7.5 and 10 mM $MgCl_2$ and stored in small aliquots at −70° C. after freezing in liquid $N_2$. Protein was determined using BCA method and bovine serum albumin as the standard.

C) [$^{125}$I]ET-1 Binding Protocol

[$^{125}$I]ET-1 binding to membranes from rat cerebellum (2–5 mg protein/assay tube) or kidney cortex (3–8 micrograms protein/assay tube) or CHO cell membranes (containing 4–6 and 1–2 micrograms of membrane protein for $ET_A$ and $ET_B$ receptors, respectively) were measured after 60 minutes incubation at 30° C. in 50 mM Tris HCl, 10 mM $MgCl_2$, 0.05% BSA, pH 7.5 buffer in a total volume of 100 microliters. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.01 nm to 50 uM.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$,5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ±S.E.M. Dissociation constants ($K_b$) of competitive antagonists were determined by the standard method of Arunlakshana and Schild. The potency range for compounds of this invention range from 0.01 nM to 50 uM.

The following examples are illustrative and are not limiting of the compounds of this invention.

EXAMPLE 1

(1RS, 2SR, 3RS)-3-[2-(2-Hydroxyeth-1-yloxy)-4-methoxyphenyl]-1-(3,4-methylenedioxyphenyl)-5-(prop-1-yloxy)indane-2-carboxylic Acid, Dicyclohexylamine Salt m.p. 182°–184° C. Anal. Calc. for $C_{41}H_{53}NO_8$:C, 71.59; H, 7.77; N, 2.04. Found: C, 71.67; H, 7.66; N, 2.42.

EXAMPLE 2

(+) (1S, 2R, 3S)-3-[2-(2-Hydroxyeth-1-yloxy)-4-methoxyphenyl]-1-(3,4-methylenedioxyphenyl)-5-propoxyindane-2-carboxylic Acid a) Benzyloxyethylbromide

A mixture of benzyl bromide (103 g, 0.60 moles) and tetrathylammonium iodide (3.1 g, 0.012 moles) under argon was heated to 145° C. Ethylene carbonate (84.5 g, 0.96 moles) was added over 0.75 hr., and the reaction mixture stirred at 145°–160° C. for 24 hrs. The mixture was cooled, diluted with 250 ml of deionized water and extracted with 2×200 ml of methylene chloride. The organic extracts were washed with brine, dried over $MgSO_4$, and concentrated in vacuo. Distillation gave 90 g (70%) of product as a light yellow liquid (b.p. 80°–85° C., 0.5 mm).

b) 1-Bromo-2-(2-benzyloxyeth-1-yloxy)-4-methoxybenzene

A mixture of 1-bromo-2-hydroxy-4-methoxy benzene (68.3 g, 0.336 moles), anhydrous potassium carbonate (51.2 g 0.37 moles) and 0.5L of N,N-dimethylformamide was heated to 65° C. Benzyloxyethylbromide (76.0 g, 0.353 moles) was added dropwise over 0.5 hr. After stirring for 1.5 hr. at 65° C., the reaction mixture was cooled and filtered. The filtrate was diluted with 1L of deionized water, and extracted with 3×0.5L ethyl acetate. The organic extracts were washed with brine, dried over MgSO$_4$, and concentrated in vacuo. Distillation gave 93 g (83%) of product as a yellow liquid (b.p. 170°–175° C., 0.5 mm).

c) Methyl(1SR)-1-hydroxyy3-[2-benzyloxyeth-1-yloxy)-4-methoxyphenyl]-1-(3,4methylene Dioxyphenyl)-5-propoxyindene-2-carboxylate A solution of 1-bromo-2-(2-benzyloxyeth-1-yloxy)-4-methoxybenzene (161 g, 0.478 moles) and 1.6L of tetrahydrofuran @–70° C. under argon was treated with n-butyl lithium (190 mL, 2.5 m, 0.478 moles), followed by magnesium bromide etherate (132 g, 0.512 moles). After stirring for 0.5 hr., a solution of methyl-3-(3,4-methylenedioxyphenyl)-5-propoxy-1-oxo-indene-2-carboxylate (117 g, 0.32 moles) in 1L of tetrahydrofuran was added over 0.5 hr. The reaction mixture was stirred for 1 hr. at –70° C., and quenched by addition of aqueous ammonium chloride. The mixture was extracted with 3×1L of methyl t-butylether. The organic extracts were washed with brine, dried over MgSO$_4$, and concentrated in vacuo to give 240 g of crude product. Chromatography on 1.5 Kg silica gel using a hexane:methylene chloride:ethyl acetate gradient gave 175 g (88%) of light orange oil.

d) Methyl (1SR, 2SR, 3SR)-3-[2-(2-hydroxyeth-1-yloxy)-4-methoxyphenyl]-1-(3,4-methylenedioxy Phenyl)-5-propoxyindane-2-carboxylate A mixture of methyl (1SR)-1hydroxy-3-[2-(2-benzyloxyeth-1-yloxy)-4-methoxyphenyl]-1-(3,4-methylenedioxy phenyl)-5-propoxyindene-2-carboxylate (88 g, 0.141 moles) 10% palladium on carbon (21 g), 0.65L of absolute ethanol and 0.65L of ethylacetate was hydrogenated at 50 psi, 55° C. for 48 hrs. The catalyst was filtered off, and the filtrate concentrated in vacuo to give an amorphous glass. Crystallization from 350 mL of absolute ethanol gave 59.5 g (81%) of white solid; m.p. 165°–168° C.

Chiral Resolution

Separation of (+) and (–) methyl (1SR, 2SR, 3SR)-3-[2-(2-hydroxyeth-1-yloxy)-4-methoxyphenyl]-1-(3,4-methylenedioxyphenyl)-5-propoxyindane-2-carboxylate was accomplished using an amylose tris (3,5-dimethylphenylcarbamate) coated on silica gel (Daicel Chiralpak AD). The mobile phase consisted of 50:40:10—hexane:isopropanol:chloroform. The retention times of the enantiomers were 4.7 min (+isomer), and 9.2 min (–isomer), using a 4.6×250 mm column at 1.0 ml/min.

e) (+) (1S, 2R, 3S)-3-[2-(2-Hydroxyeth-1-yloxy)-4-methoxyphenyl]-1-(3,4-methylenedioxyphenyl)-5-propoxyindane-2-carboxylic Acid To a solution of (+) methyl (1S, 2S, 3S)-3-[2-(2-hydroxyeth-1-yloxy)-4-methoxyphenyl]-1-(3,4-methylenedioxyphenyl)-5-propoxyindane-2-carboxylate (69.3 g, 0.133 moles) in 1.4L of methanol and 0.14L of deionized water was added 50% aqueous sodium hydroxide (0.059L, 0.74 moles). The reaction mixture was refluxed for 16 hrs. After concentrating the mixture in vacuo, the slurry was diluted with 1L of deionized water, and acidified to pH 2 with 3 N HCl. The mixture was extracted with 3×500mL of methyl-t-butyl ether. The organic extracts were combined, washed with brine, dried of MgSO$_4$, and concentrated in vacuo. The resulting oil was crystallized from 400 mL of isopropanol to give 40.7 g (60%) of white solid; m.p. 119°–122° C.; $[\alpha]_D^{24°\ C.}$ =+60.4° (C=0.5, CH$_3$OH).

Formation of the hemiethylenediamine salt gave a white crystalline solid; m.p. 177°–179° C.; $[\alpha]_D^{24°\ C.}$ =+70.0° (C=0.5, CH$_3$OH).

EXAMPLE 3

(1RS, 2SR, 3RS)-3-[2-(2-Hydroxyeth-1-yloxy)-4-methoxyphenyl]-1-(3,4-methylenedioxyphenyl)-5-(prop-1-yloxy)indan-2-yl acetic acid, mp 139°–146°.

EXAMPLE 4

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

| Procedure for tablets: | |
|---|---|
| Step 1 | Blend ingredients No. 1, No. 2, No. 3 and No. 4 in a suitable mixer/blender. |
| Step 2 | Add sufficient water portion-wise to the blend from Step 1 with careful mixing after each addition. Such additions of water and mixing until the mass is of a consistency to permit its conversion to wet granules. |
| Step 3 | The wet mass is converted to granules by passing it through an oscillating granulator using a No. 8 mesh (2.38 mm) screen. |
| Step 4 | The wet granules are then dried in an oven at 140° F. (60° C.) until dry. |
| Step 5 | The dry granules are lubricated with ingredient No. 5. |
| Step 6 | The lubricated granules are compressed on a suitable tablet press. |

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A method of treating pulmonary hypertension which comprises administering to a subject in need thereof a compound of Formula (I):

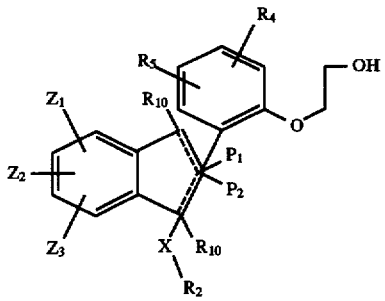

(I)

wherein:

$R_2$ is a moiety of formula (a) or (b);

$P_1$ is $CO_2H$, $C(R_6)_2CO_2H$ or tetrazole;

$P_2$ is hydrogen;

$R_3$ and $R_5$ are independently, OH, $C_{1-8}$alkoxy, $N(R_6)_2$, Br, F, I, Cl, $R_{13}CO_2R_7$, —X—$R_9$—Y, NH (CO)$CH_3$, $OC_{1-4}$alkylphenyl, $[S(O)_pC_{1-5}$alkyl]$S(O)_qC_{1-5}$alkyl or —$X(CH_2)_nR_8$;

$R_4$ is hydrogen, OH, $C_{1-5}$alkoxy, $N(R_6)_2$, Br, F, I, Cl, $C_{1-4}$alkyl, NH(CO)$CH_3$, or $S(O)_qC_{1-5}$alkyl wherein the $C_{1-5}$alkoxy may be unsubstituted or substituted by OH, methoxy, Br, F, I or Cl;

$R_6$ is independently hydrogen or $C_{1-4}$alkyl;

$R_7$ is independently hydrogen, $C_{1-10}$alkyl, $C_{2-10}$alkenyl or $C_{2-8}$alkynyl, all of which may be unsubstituted or substituted by one or two OH, $N(R_6)_2$, $CO_2R_{12}$, Br, Cl, I, F or $XC_{1-5}$alkyl; or $R_7$ is $(CH_2)_nAr$;

$R_8$ is independently phenyl, pyridyl, hydrobenzofuranyl, benzodioxanyl, all of which may be unsubstituted or substituted by one or two $CO_2R_7$, OH, $CH_2OH$, $N(R_6)_2Br$, Cl, F or I; hydrogen, $CO_2R_7$, $CO_2C(R_7)_2O(CO)XR_7$, $PO_3(R_7)_2$, $SO_2N(R_7)_2$, $SO_2NR_7R_{11}$, $NR_7SO_2R_{11}$, $CONR_7SO_2R_{11}$, $SO_3R_7$, $SO_2C_{1-10}$alkyl, $P(O)(OR_7)R_7$, CN, —$CO_2(CH_2)_mC(O)N(R_6)_2$, $C(R_{11})_2N(R_7)_2$, $C(O)N(R_6)_2$, tetrazole or $OR_6$; or $C_{1-8}$alkyl, $C_{2-8}$alkenyl, $C_{2-8}$alkynyl, all of which may be unsubstituted or substituted by one or two OH, $CH_2OH$, $N(R_6)_2$ Br, Cl, F or I; with the proviso that $R_{11}$ is not hydrogen when part of a $SO_2R_{11}$ group.

$R_9$ is a bond, $C_{1-10}$alkylene, $C_{2-10}$alkenylene, $C_{2-10}$alkylidene, $C_{2-10}$alkynylene, all of which may be linear or branched, or phenylene, all of which may be unsubstituted or substituted by one or more OH, $N(R_6)_2$, COOH Br, F, Cl or I;

$R_{10}$ is hydrogen;

$R_{11}$ is hydrogen, phenyl, benzodioxanyl or pyridyl, all of which may be substituted or unsubstituted by one or two $C_{1-4}$ alkyl groups; $C_{1-8}$alkyl, $C_{2-8}$alkenyl, $C_{2-8}$alkynyl, all of which may be unsubstituted or substituted by one or two OH, $CH_2OH$, $N(R_6)_2$ Br, Cl, F or I;

$R_{12}$ is hydrogen, $C_{1-6}$alkyl, $C_{2-6}$alkenyl or $C_{2-7}$alkynyl;

$R_{13}$ is phenylene, pyridylene, $C_{1-10}$ alkylene, $C_{1-10}$alkylidene, $C_{2-10}$alkenylene, $C_{2-10}$alkynylene, all of which may be unsubstituted or substituted by one or two OH, $CH_2OH$, $N(R_6)_2$ Br, Cl, F or I;

X is independently $(CH_2)_n$ or O;

Y is $CH_3$ or $X(CH_2)_nAr$;

Ar is:

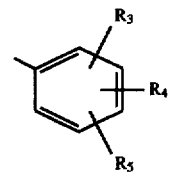

(a)

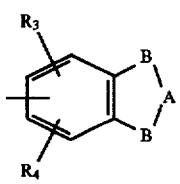

(b)

or indolyl, pyridyl, which may be unsubstituted or substituted by one or two $R_3$ or $R_4$ groups;

A is C=O, or $(C(R_6)_2)_m$;

B is independently —$CH_2$— or —O—;

$Z_1$, $Z_2$ and $Z_3$ are independently hydrogen, OH, $C_{1-8}$alkoxy, $S(O)qC_{1-8}$alkyl, $N(R_6)_2$, Br, F, I, Cl, $NHCOR_6$, —X—$R_9$—Y, —$X(CH_2)_nR_8$, or $Z_1$ and $Z_2$ together may be —O—A—O— on contiguous carbons;

q is zero, one or two;

n is an integer from 0 to six;

m is 1, 2 or 3; and the dotted line indicates the optional presence of a double bond; or a pharmaceutically acceptable salt thereof; provided that when the optional double bond is present there is only one $R_{10}$ and there is no $P_1$; and when $R_3$, $R_5$, $Z_1$, $Z_2$, or $Z_3$ is $X(CH_2)_nR_8$ and n is not 0, X is oxygen when $R_8$ is $OR_6$ or $CO_2H$.

2. A method of treatment of claim 1 wherein $R_3$ is hydrogen, —$X(CH_2)_nR_8$ or $R_{13}CO_2R_7$; $R_5$ is hydrogen, OH, $C_{1-5}$alkoxy, $SC_{1-5}$alkyl, substituted phenyl or pyridyl, F, Br, $C_{1-3}$alkyl or $NH_2$; $R_4$ is hydrogen, OH, or $C_{1-5}$alkoxy; $Z_1$ and $Z_3$ are hydrogen and $Z_2$ is hydrogen, OH, $C_{1-5}$alkoxy, Br, Cl, F, I, $X(CH_2)_nR_8$, $NH_2$, or NH(CO)$CH_3$, or $Z_1$ and $Z_2$ together may be O—A—O on contiguous carbons.

3. A method of treatment of claim 2 wherein there is no optional double bond; $Z_2$ is hydrogen, OH, or $C_{1-5}$alkoxy, $Z_1$ is hydrogen; $R_3$ is hydrogen, XAr, $X(CH_2)_nCO_2H$, $X(CH_2)_nCONR_7SO_2R_{11}$, $X(CH_2)_nOR_6$ or CH=CHCO$_2$H, $R_5$ is hydrogen, substituted phenyl or pyridyl, or $C_{1-2}$alkoxy; $R_4$ is hydrogen and $P_1$ is $CO_2H$ or —$C(R_6)_2CO_2H$.

4. A method of treatment of claim 3 wherein $R_2$ is a moiety of formula (a) or (b); A is $CH_2$, B is —O—; there is no optional double bond; X is a bond in $XR_2$; $Z_1$ and $Z_3$ are hydrogen; $Z_2$ is hydrogen, OH, or $C_{1-5}$alkoxy; $R_3$ is hydrogen, OAr or $OCH_2Ar$ (where Ar is (a), (b) or pyridyl and A is $CH_2$ and B is —O— and Ar may be substituted by $CO_2H$, $O(CH_2)_{1-3}CO_2H$, —$O(CH_2)_{1-3}CONHSO_2R_{11}$, $(CH_2)_{0-4}CO_2H$, $(CH_2)_{0-3}CONH$-$SO_2R_{11}$, or O{$(CR_6)_2$}$_{2-4}$, OH; $R_5$ is hydrogen, $C_{1-2}$alkoxy, or phenyl or pyridyl or all of which may be substituted by $R_3$ or $C_{1-2}$alkoxy; $R_4$ is hydrogen; and $P_1$ is $CO_2H$ or $CH_2CO_2H$.

5. A method of claim 1 wherein the compound is selected from the group consisting of:

(1RS, 2SR, 3RS)-3-[2-(2-Hydroxyeth-1-yloxy)-4-methoxyphenyl]-1-(3,4-methylenedioxyphenyl)-5-(prop-1-yloxy)indane-2-carboxylic acid, and (1RS, 2SR, 3RS)-3-[2-(2-Hydroxyeth-1-yloxy)-(4-methoxyphenyl)]-1-(3,4-methylenedioxyphenyl)-5-(prop-1-yloxy)indan-2-yl acetic acid.

6. A method of claim 1 wherein the compound is:

(+)(1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid.

7. A method of claim 1 wherein the compound:

(+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylate hemiethylenediamine salt.

* * * * *